United States Patent [19]

L'Italien et al.

[11] 4,145,347

[45] Mar. 20, 1979

[54] N-(SUBSTITUTED-AMINOALKYL)-2-oxo-1-PYRROLIDINEACETAMIDES

[75] Inventors: Yvon J. L'Italien, Plymouth; Ivan C. Nordin, Ann Arbor, both of Mich.

[73] Assignee: Parke, Davis & Company, Detroit, Mich.

[21] Appl. No.: 884,464

[22] Filed: Mar. 7, 1978

Related U.S. Application Data

[63] Continuation-in-part of Ser. No. 773,877, Mar. 3, 1977, abandoned.

[51] Int. Cl.$^2$ ............................................. C07D 207/26
[52] U.S. Cl. ............................... 546/208; 260/326.43; 544/372; 544/141; 424/248.54; 424/250; 424/267; 424/274; 546/246
[58] Field of Search ...................... 260/293.71, 326.43; 544/141, 372

[56] References Cited

U.S. PATENT DOCUMENTS

| 2,744,930 | 5/1956 | Krapcho | 260/326.43 |
| 3,509,171 | 4/1970 | Welstead et al. | 544/141 |

FOREIGN PATENT DOCUMENTS

| 1011886 | 7/1957 | Fed. Rep. of Germany | 260/326.43 |
| 2507576 | 9/1975 | Fed. Rep. of Germany | 260/326.43 |

*Primary Examiner*—Natalie Trousof
*Assistant Examiner*—Robert T. Bond
*Attorney, Agent, or Firm*—Stephen Raines; David B. Ehrlinger; Frank S. Chow

[57] ABSTRACT

N-(substituted-aminoalkyl)-2-oxo-1-pyrrolidineacetamides which are useful as pharmacological agents, especially cognition activators, are disclosed. They can be produced by reacting a 2-oxo-1-pyrrolidineacetate ester with an appropriate amine.

12 Claims, No Drawings

N-(SUBSTITUTED-AMINOALKYL)-2-OXO-1-PYRROLIDINEACETAMIDES

This application is a continuation-in-part of copending application Ser. No. 773,877, filed March 3, 1977, now abandoned

SUMMARY AND DETAILED DESCRIPTION

The present invention relates to new N-(substituted-aminoalkyl)-2-oxo-1-pyrrolidineacetamides. More particularly, the invention relates to new N-(substituted-aminoalkyl)-2-oxo-1-pyrrolidineacetamides of the formula

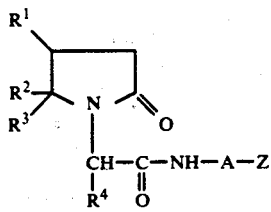

and acid addition salts thereof, and to a method for the production of the foregoing compounds; where $R^1$ is hydrogen or phenyl, $R^2$, $R^3$ and $R^4$ are hydrogen or methyl, A is an alkylene chain having two, three or four carbon atoms which is optionally substituted with one or two methyl or ethyl groups and Z is di(lower alkyl)amino, 4-morpholinyl, 4-(lower alkyl)-1-piperazinyl or (lower alkyl)$_n$-piperidinyl where n is an integer from zero to six with the proviso that when $R^1$ is phenyl, $R^2$ and $R^3$ are hydrogen. The preferred compounds are those wherein A is ethylene or trimethylene, $R^1$ to $R^4$ are hydrogen and Z is 2,6-dimethyl-1-piperidinyl or di(lower alkyl)amino.

The term "lower alkyl" is intended to mean an alkyl group of from one to four carbon atoms.

The term "acid addition salts" are intended to mean salts formed by the addition of an acid. Typical salts are as follows: pamoate, acetate, citrate, hydrochloride, sulfate, phosphate, benzoate, etc. Pharmaceutically acceptable acid addition salts are preferred.

The compounds of this invention are intended to encompass all of the possible stereo chemical forms of the compounds. In addition, the compounds are intended to include hydrates or solvates.

In accordance with the invention, the foregoing compounds of formula I can be prepared by reacting a compound of the formula

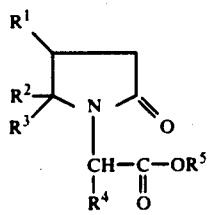

with a compound of the formula

H$_2$N-A-Z      III where $R^1$ through $R^4$, A and Z are as previously defined for formula I and $R^5$ is a lower alkyl group.

The foregoing reaction is preferably conducted in the absence of any solvent; however a solvent may be employed. A solvent such as a hydrocarbon (benzene, toluene or xylene) or an ether (dioxane, tetrahydrofuran or diethylene glycol dimethyl ether) may be used or a mixture thereof. While preferably an excess of the amine formula III is used (up to 50 percent) approximately equimolar quantities of the two reactants may be employed. The above reaction is generally conducted at a temperature of from 50° to 175° C. for a period of from 12 to 36 hours, preferably 90° to 150° C. for from 16 to 24 hours. The products may be isolated by conventional means such as distillation and/or crystallization. In addition, the product may be isolated in the form of an acid addition salt by reaction with an appropriate acid. The compounds of this invention are bases or the corresponding acid addition salts of these bases. The bases and their acid addition salts may be conveniently converted from one form to the other by using an appropriate acid or base.

The starting materials of the formula II are prepared by reacting a compound of the formula

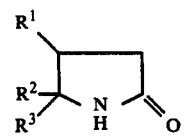

with a compound of the formula

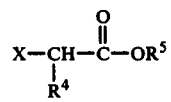

in the presence of sodium hydride where $R^1$, $R^2$, $R^3$, $R^4$ and $R^5$ are as previously defined and X is chloro or bromo.

Compounds of the formulae IV and V are known compounds.

Compounds of the formula III are prepared by reducing the cyano function of compounds of the formula Z-(CR$^6$R$^7$)$_n{}^1$CN using either LiAlH$_4$ or hydrogen (RaCo), where Z is as previously defined, $R^6$ and $R^7$ are hydrogen, methyl or ethyl and $n^1$ is an integer from one to three.

Compounds of the formula

Z-(CR$^6$R$^7$)$_n{}^1$CN are prepared by reacting a compound of the formula

ZH with compounds of the formulae

H$_2$C=CHCN, HOCR$^6$R$^7$CN and Br(CR$^6$R$^7$)$_n{}^1$CN where Z, $R^6$, $R^7$ and $n^1$ are as previously defined.

The compounds of the invention can exist in anhydrous form as well as in solvated, including hydrated, forms. In general, the hydrated forms and the solvated forms with pharmaceutically-acceptable solvents are equivalent to the anhydrous or unsolvated form for the purposes of the invention. In addition, they can exist in racemic form as well as in optically active d- and l-forms. Lastly, certain of the compounds of this invention can exist in cis or trans forms. This invention is intended to include all of these isomeric forms.

The compounds of the invention are new chemical compounds of value as pharmacological agents. More specifically, they are cognition activators which are potentially useful in treating patients suffering from senility. The compounds also find use in the treatment of induced amnesia. In addition, the alerting and attention focusing quality of these compounds would make them useful in treating patients having certain learning disabilities.

The compounds of this invention may be administered orally in the form of tablets, capsules, syrups, etc. or parenterally by being dissolved in an appropriate isotonic solution.

The effectiveness of the aforementioned compounds is determined by the test given below which is designed to show the compounds ability to reverse amnesia produced by an electroconvulsive shock.

One hundred male mice (Carworth, CF-1 strain, 19-21 g. at time of shipment) are divided into five groups of 20 mice each. Each mouse is placed, one at a time, on a small shelf attached to the outside wall of a test box. In this position the mouse is suspended in space. Therefore, the mouse is motivated to step from the shelf through a conveniently place small hole into the interior of the box. As soon as the mouse has all four feet within the semidarkened interior of the box, the grid floor of the box is electrified (1.5 milliamps, 3 second duration) to produce a strong pain-fear reaction from the animal. About five seconds thereafter, the mouse is removed from the test box and placed in a group holding cage.

Two hours after the above training the mice are given a single electroconvulsive shock produced by 20 milliamps delivered for 0.5 seconds through the ears. Immediately thereafter, the mice are returned to the holding cage.

Two hours after the convulsive treatment, the mice are injected intraperitoneally with the chemical being assessed. Usually three doses of the chemical will be tested at a time.

One hour after the drug treatment, the mice are tested for memory of the painful foot shock received within the shelf-box apparatus. This testing is accomplished by once again placing each mouse on the small shelf attached to the test box. Any mouse that stays on the shelf for 60 seconds without entering the box is counted as remembering the painful foot shock received within the box five hours earlier. Any mouse entering the box within the 60-second period is counted as having amnesia for the painful event.

Using this 60-second criterion, appropriate control experiments show (1.) 100 percent of mice will enter the box if no foot shock is delivered during the original training, (painful foot shock is necessary if the mice are to develop an aversion to entering the test box) (2.) 100 percent of mice will enter the box under the foregoing conditions even when treated with electroconvulsive shock at the three-hour point prior to testing (electroconvulsive shock treatment itself does not generate a fear of entering the test box).

The five groups of mice are treated as follows:

| Group | Treatments |
|---|---|
| 1) Ceiling Control Group: | Placebo |
| 2) Base Line Control Group: | Electroconvulsive shock, Placebo |
| 3) 1st Drug Dose Group: | Electroconvulsive shock, N-(substituted-aminoalkyl)-2-oxo-1-pyrrolidineacetamide |
| 4) 2nd Drug Dose Group: | Electroconvulsive shock, N-(substituted-aminoalkyl)-2-oxo-1-pyrrolidineacetamide |
| 5) 3rd Drug Dose Group: | Electroconvulsive shock, N-(substituted-aminoalkyl)-2-oxo-1-pyrrolidineacetamide |

The percentage of amnesia reversal is determined as follows for each drug group:

$$\text{percent amnesia reversal} = \frac{\text{Drug group} - \text{Base line control group}}{\text{Ceiling control group} - \text{Base line control group}} \times 100$$

The following criteria is used in interpreting the precent of amnesia reversal scores:

40 percent or more (active) 25 to 39 percent (boarderline) and 0 to 29 percent (inactive). The following table reports the results for certain compounds of the invention.

ACTIVITY TABLE $$\begin{array}{c} R^1 \\ R^2 \diagdown \diagup \\ R^3 \diagup \quad N \diagdown \\ \quad | \quad \quad \diagup O \\ CH-C-NH-A-Z \\ | \quad \| \\ R^4 \quad O \end{array}$$

| | | | | | | \% Amnesia Reversal at Indicated Dose, mg/kg in Mice | | | | | | | |
|---|---|---|---|---|---|---|---|---|---|---|---|---|---|
| $R^1$ | $R^2$ | $R^3$ | $R^4$ | A | Z | 160 | 80 | 40 | 20 | 5.0 | 2.5 | 1.25 | 0.63 |
| H | H | H | H | —(CH$_2$)$_2$— | CH$_3$—N⟨piperidine⟩—CH$_3$ | | 10 | | 70 | 70 | 50 | 20 | 10 |
| H | H | H | H | —(CH$_2$)$_3$— | —N(CH$_3$)$_2$ | | | 46 | | 46 | 31 | | |
| H | H | H | H | —(CH$_2$)$_2$— | —N(C$_2$H$_5$)$_2$ | | | 31 | | 46 | 15 | | |

ACTIVITY TABLE-continued
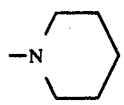
| R¹ | R² | R³ | R⁴ | A | Z | % Amnesia Reversal at Indicated Dose, mg/kg in Mice | | | | | | | |
|---|---|---|---|---|---|---|---|---|---|---|---|---|---|
| | | | | | | 160 | 80 | 40 | 20 | 5.0 | 2.5 | 1.25 | 0.63 |
| H | H | H | H | —(CH₂)₂— |  | | 0 | 0 | 45 | 45 | 64 | 18 | |
| H | H | H | H | —(CH₂)₂— | —N[CH(CH₃)₂]₂ | | 18 | 82 | 96 | 60 | 30 | 0 | |
| C₆H₅— | H | H | H | —(CH₂)₂— | —N(C₂H₅)₂ | | 8 | 0 | 42 | 27 | 0 | 0 | |
| C₆H₅— | H | H | H | —(CH₂)₃— | —N[CH(CH₃)₂]₂ | | 27 | 55 | 82 | 45 | 0 | 9 | |
| H | H | H | H | —(CH₂)₂ | —N[CH₂CH(CH₃)₂]₂ | | 15 | | 23 | 54 | 33 | 25 | |
| H | H | H | H | —(CH₂)₃— | 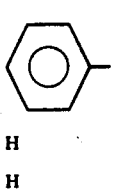 | 60 | 100 | 70 | 55 | 50 | 33 | 25 | |
| H | H | H | H | —CH₂C(CH₃)₂— | 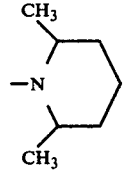 | 45 | 55 | 73 | 27 | 18 | | | |
| H | H | H | H | —(CH₂)₂— | —N(CH₃)₂ . HCl | | 33* | 40* | 56* | 50 22* | | | |
| H | H | H | H | —(CH₂)₂— | —N(CH₃)[CH(CH₃)₂] | | | | | | | | |
| H | CH₃ | H | H | —(CH₂)₂ | 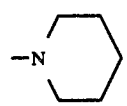 | | 0 | 36 | 55 | 67 | 58 | 33 | |
| H | CH₃ | CH₃ | H | —(CH₂)₃ | 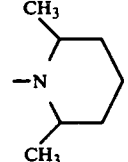 | 33 | 50 | 58 | 58 | 25 | | | |
| C₆H₅— | H | H | H | —(CH₂)₂— | 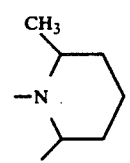 | | 33 | 44 | 67 | 40 | 10 | 0 | |
| H | H | H | H | —CH₂CH(CH₃)— | 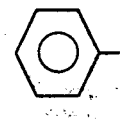 | | 15 | 46 | 15 | | | | |

ACTIVITY TABLE-continued

Structure:

$$\text{pyrrolidinone with substituents } R^1, R^2, R^3 \text{ on ring, N-CH(R^4)-C(=O)-NH-A-Z}$$

| R¹ | R² | R³ | R⁴ | A | Z | 160 | 80 | 40 | 20 | 5.0 | 2.5 | 1.25 | 0.63 |
|---|---|---|---|---|---|---|---|---|---|---|---|---|---|
| H | CH₃ | H | H | —CH₂CH(CH₃)— | —N(piperidinyl) | | 45 | | 36 | 18 | | | |
| H | CH₃ | H | H | —(CH₂)₂— | —N[CH(CH₃)₂]₂ | | 56 | | 0 | 0 | | | |
| H | CH₃ | CH₃ | H | —(CH₂)₂— | 2,6-dimethylpiperidinyl | 80 | 44 | 40 | 22 | | | | |
| H | H | H | H | —(CH₂)₃— | morpholinyl | 54 | 58 | 31 | 17 | 0 | | | |
| H | H | H | H | —(CH₂)₃— | 2,4,6-trimethylpiperidinyl | | 45 | | 18 | 9 | | | |
| H | H | H | H | —(CH₂)₃— | 4-methylpiperazinyl | 38 | 69 | 69 | 27 | 9 | 0 | | |
| H | H | H | CH₃ | —(CH₂)₂— | 2,6-dimethylpiperidinyl | | 61 | | 42 | 17 | | | |
| H | H | H | CH₃ | —(CH₂)₃— | 2,6-dimethylpiperidinyl | | 30 | | 23 | 50 | 8 | | |

% Amnesia Reversal at Indicated Dose, mg/kg in Mice

*after 1 second electroconvulsive shock.

The invention is further illustrated by the following examples:

EXAMPLE 1

A mixture of 17.1 g. of ethyl 2-oxo-1-pyrrolidineacetate (U.S. Pat. No. 3,459,738) and 25.4 g. of cis-2-(2,6-dimethyl-1-piperidinyl)ethylamine (U.S. Pat. No. 3,446,811) is heated at 95°-100° C. for 16 hours. The excess cis-2-(2,6-dimethyl-1-piperidinyl)ethylamine is evaporated at reduced pressure and the residue is fractionated. The product, cis-N-[2-(2,6-dimethyl-1-piperidinyl)ethyl]-2-oxo-1-pyrrolidineacetamide, is obtained as an oil, b.p. 178°-183° C./0.15 mm., which crystallizes on standing; m.p. 93°-94.5° C. after two crystallizations from ethyl acetate-pentane.

A solution of 27.5 g. of the above base product in 150 ml. of acetonitrile is cooled to 0°-5° C. and an excess of dry hydrogen chloride is bubbled in. The excess hydrogen chloride is destroyed by the addition of sufficient ethylene oxide. The resulting solution is diluted with ether, seeded, and allowed to crystallize. The hydrochloride salt is collected by filtration and recrystallized from 2-propanol-ether; m.p. 166°–167° C.

EXAMPLE 2

From 12.8 g. of ethyl 2-oxo-1-pyrrolidineacetate and 15.3 g. of 3-(dimethylamino)propylamine (U.S. Pat. No. 2,459,080), following the procedure of Example 1, there is obtained N-[3-(dimethylamino)propyl]-2-oxo-1-pyrrolidineacetamide; b.p. 157°–159° C./0.15 mm.

EXAMPLE 3

From 12.8 g. of ethyl 2-oxo-1-pyrrolidineacetate and 17.4 g. of 2-(diethylamino)ethylamine [J.A.C.S. 68, 2006 (1946)], following the procedure of Example 1, there is obtained N-[2-(diethylamino)ethyl]-2-oxo-1-pyrrolidineacetamide; b.p. 157° C./0.1 mm.

EXAMPLE 4

From 12.8 g. of ethyl 2-oxo-1-pyrrolidineacetate and 19.2 g. of 2-(1-piperidinyl)ethylamine [Compt. rend. 233, 1121 (1951)], following the procedure of Example 1, there is obtained 2-oxo-N-[2-(1-piperidinyl)ethyl]-1-pyrrolidineacetamide; b.p. 185°–187° C./0.15 mm.

EXAMPLE 5

From 17.1 g. of ethyl 2-oxo-1-pyrrolidineacetate and 21 g. of 2-(diisopropylamino)ethylamine [J.A.C.S. 78, 486 (1956)], following the procedure of Example 1, there is obtained N-[2-[bis(1-methylethyl)amino]ethyl]-2-oxo-1-pyrrolidineacetamide; b.p. 164° C./0.15 mm.

EXAMPLE 6

From 7.0 g. of methyl 2-oxo-4-phenyl-1-pyrrolidineacetate and 5.0 g of 2-(diethylamino)ethylamine, following the procedure of Example 1, there is obtained N-[2-(diethylamino)ethyl]-2-oxo-4-phenyl-1-pyrrolidineacetamide in pure form as an oil, without need for distillation.

(a) Methyl 2-oxo-4-phenylpyrrolidineacetate

A total of 8.4 g. of 57% sodium hydride dispersion in mineral oil is washed successively with 200 ml. portions of toluene to remove the mineral oil. The residual sodium hydride is suspended in 600 ml. of tetrahydrofuran and the suspension is treated portionwise, with stirring, with 32.8 g. of 4-phenyl-2-pyrrolidinone (C.A. 53:4253 g.). Upon completion of the addition, the stirred mixture is heated in the range of 35°–65° C. from one to three hours (monitoring hydrogen evolution), followed by the dropwise addition of 21.8 g. of methyl chloroacetate. After stirring for about 16 hours at 55°–65° C. to insure completeness of reaction, the mixture is cooled and evaporated at reduced pressure. The residue is mixed with 200 ml. of water and extracted twice with 200 ml. portions of ether. The combined ether extract is dried, evaporated and fractionated at reduced pressure. Methyl 2-oxo-4-phenyl-1-pyrrolidineacetate is obtained as an oil, b.p. 158°–159° C./0.15 mm.

EXAMPLE 7

From 6.2 g. of methyl 2-oxo-4-phenylpyrrolidineacetate and 8.0 g. of 3-(diisopropylamino)propylamine [J.A.C.S. 65, 2012 (1943)], following the procedure of Example 1, there is obtained N-[3-[bis(1-methylethyl)amino]propyl]-2-oxo-4-phenyl-1-pyrrolidineacetamide in pure form as an oil, without need for distillation.

EXAMPLE 8

From 8.5 g. of ethyl 2-oxo-1-pyrrolidineacetate and 12.9 g. of 2-(diisobutylamino)ethylamine (British Pat. No. 614,164), following the procedure of Example 1, there is obtained N-[2-[bis(2-methylpropyl)amino]ethyl]-2-oxo-1-pyrrolidineacetamide; b.p. 155°–160° C./0.1 mm.

EXAMPLE 9

A mixture of 8.5 g. of ethyl 2-oxo-1-pyrrolidineacetate and 9.4 g. of cis-3-(2,6-dimethyl-1-piperidinyl)propylamine (U.S. Pat. No. 3,446,811) is heated at 95°–100° C. under nitrogen and an air condenser plugged with cotton for 20 hours. The excess cis-3-(2,6-dimethyl-1-piperidinyl)propylamine is evaporated at reduced pressure and the residue is cooled to crystallize the product, cis-N-[3-(2,6-dimethyl-1-piperidinyl)propyl]-2-oxo-1-pyrrolidineacetamide; m.p. 69°–70° C. after recrystallization from heptane and hexane. (The product can also be purified by distillation at reduced pressure; b.p. 185° C./0.1 mm).

A solution of 27.5 g. of the above product in 150 ml. of acetonitrile is cooled to 0°–5° C. and an excess of dry hydrogen chloride gas is introduced. The excess hydrogen chloride is destroyed by the addition of sufficient ethylene oxide. The resulting solution is diluted with ether, seeded, and allowed to crystallize. The hydrochloride salt is collected by filtration and recrystallized from 2-propanol-ether; m.p. 152°–153° C.

EXAMPLE 10

From 8.56 g. of ethyl 2-oxo-1-pyrrolidineacetate and 12.5 g. of 2-methyl-2-(1-piperidinyl)propylamine [J.A.C.S. 68, 13 (1946)], following the procedure of Example 9, there is obtained N-[2-methyl-2-(1-piperidinyl)propyl]-2-oxo-1-pyrrolidineacetamide; m.p. 69° C. after crystallization from heptane.

EXAMPLE 11

From 9.26 g. of ethyl 2-methyl-5-oxo-1-pyrrolidineacetate (British Pat. No. 1,309,692) and 8.6 g. of cis-2-(2,6-dimethyl-1-piperidinyl)ethylamine, following the procedure of Example 9, there is obtained cis-N-[2-(2,6-dimethyl-1-piperidinyl)ethyl]-2-methyl-5-oxo-1-pyrrolidineacetamide; m.p. 115°–116° C. after crystallization from cyclohexane.

EXAMPLE 12

From 10 g. of ethyl 2,2-dimethyl-5-oxopyrrolidineacetate, (British Pat. No. 1,309,692) and 10.5 g. of cis-3-(2,6-dimethyl-1-piperidinyl)propylamine, following the procedure of Example 9, there is obtained cis-N-[3-(2,6-dimethyl-1-piperidinyl)propyl]-2,2-dimethyl-5-oxo-1-pyrrolidineacetamide; m.p. 86°–87° C. after crystallization from isooctane.

EXAMPLE 13

From 7.0 g. of methyl 2-oxo-4-phenyl-1-pyrrolidineacetate and 5.0 g. of cis-2-(2,6-dimethyl-1-piperidinyl)ethylamine, following the procedure of Example 9, there is obtained cis-N-[2-(2,6-dimethyl-1-piperidinyl)ethyl]-2-oxo-4-phenyl-1-pyrrolidineacetamide; m.p. 115°–116° C. after recrystallization from cyclohexane.

EXAMPLE 14

From 7.0 g. of ethyl 2-oxo-1-pyrrolidineacetate and 6.3 g. of 2-(4-methyl-1-piperazinyl)propylamine, following the procedure of Example 9, there is obtained (±)-N-[2-(4-methyl-1-piperazinyl)propyl]-2-oxo-1-pyrrolidineacetamide; m.p. 84°–85° C. after recrystallization from cyclohexane and from heptane.

(a) 2-(4-Methyl-1-piperazinyl)propionitrile

Lactonitrile (71.08 g.) is added in a dropwise manner to a stirred solution of 100.1 g. of 1-methyl-piperazine in 500 ml. of benzene. The resulting warm solution is heated at reflux under a water separator until the theoretical amount of water is collected (about 4 hours). The solution is evaporated at reduced pressure and the residue is fractionated. The product, 2-(4-methyl-1-piperazinyl)propionitrile, is obtained as an oil, b.p. 128°–130° C./23 mm.

(b) 2-(4-Methyl-1-piperazinyl)propylamine 2-(4-Methyl-1-piperazinyl)propionitrile (38.3 g.) in 50 ml. of dry ether is added in a dropwise manner to a stirred solution of 19 g. of lithium aluminum hydride in 600 ml. of dry ether. The resulting mixture is heated at reflux for 1 hour, cooled and treated in sequence with 10 ml. of water, 7.5 ml. of 20% aqueous sodium hydroxide, and 35 ml. of water. The mixture is filtered and the filtrate is evaporated. The residue is fractionated at reduced pressure to give 2-(4-methyl-1-piperazinyl)propylamine as an oil, b.p. 92°–93° C./9 mm.

EXAMPLE 15

From 9.3 g. of ethyl 2-methyl-5-oxo-1-pyrrolidineacetate and 10.7 g. of 2-(1-piperidinyl)propylamine (J. Chem. Soc. 1947, 1511), following the procedure of Example 9, there is obtained (±)-2-methyl-5-oxo-N-[2-(1-piperidinyl)propyl]-1-pyrrolidineacetamide; m.p. 111°–112° C. after recrystallization from heptane.

EXAMPLE 16

From 9.2 g. of ethyl 2-methyl-5-oxo-1-pyrrolidineacetate and 8.7 g. of 2-(diisopropylamino)ethylamine, following the procedure of Example 9, there is obtained N-[2-[Bis(1-methylethyl)amino]ethyl]-2-methyl-5-oxo-1-pyrrolidineacetamide; m.p. 73°–74° C. after recrystallization from hexane.

EXAMPLE 17

From 10 g. of ethyl 2,2-dimethyl-5-oxo-1-pyrrolidineacetate and 11 g. of cis-2-(2,6-dimethyl-1-piperidinyl)ethylamine, following the procedure of Example 9, there is obtained cis-N-[2-(2,6-dimethyl-1-piperidinyl)ethyl]-5,5-dimethyl-2-oxo-1-pyrrolidineacetamide as the hemihydrate; m.p. 94°–94.5° C. after recrystallization from isooctane.

EXAMPLE 18

From 8.5 g. of ethyl 2-oxo-1-pyrrolidineacetate and 8.2 g. of 3-(4-morpholinyl)propylamine [J.A.C.S. 63, 156 (1941)], following the procedure of Example 9, there is obtained N-[3-(4-morpholinyl)propyl]-2-oxo-1-pyrrolidineacetate; m.p. 101°–102° C. after recrystallization from isooctane.

EXAMPLE 19

From 8.5 g. of ethyl 2-oxo-1-pyrrolidineacetate and 14 g. of 3-(2,2,4,6-tetramethyl-1-piperidinyl)propylamine (U.S. Pat. No. 3,446,811), following the procedure of Example 9, there is obtained N-[3-(2,2,4,6-tetramethyl-1-piperidinyl)propyl]-2-oxo-1-pyrrolidineacetamide; m.p. 85°–87° C. after recrystallization from ethyl ether.

EXAMPLE 20

From 8.5 g. of ethyl 2-oxo-1-pyrrolidineacetate and 10.2 g. of 3-(4-methyl-1-piperazinyl)propylamine [J.A.C.S. 82, 2386 (1960)], following the procedure of Example 9, there is obtained N-[3-(4-methyl-1-piperazinyl)propyl]-2-oxo-1-pyrrolidineacetamide; m.p. 93° C. after recrystallization from cyclohexane.

EXAMPLE 21

A mixture of 9.25 g. of ethyl α-methyl-2-oxo-1-pyrrolidineacetate (British Pat. No. 1,309,692) and 11.2 g. of cis-2-(2,6-dimethyl-1-piperidinyl)ethylamine is heated under nitrogen and an air condenser plugged with cotton for 20 hours at 150° C. The excess cis-2-(2,6-dimethyl-1-piperidinyl)ethylamine is evaporated at reduced pressure and the residue is fractionated. The product, cis-(±)-N-[2-(2,6-dimethyl-1-piperidinyl)ethyl]-α-methyl-2-oxo-1-pyrrolidineacetamide, is obtained as an oil, b.p. 168°–170° C./0.1 mm.

EXAMPLE 22

From 9.25 g. of ethyl α-methyl-2-oxo-1-pyrrolidineacetate and 10.5 g. of cis-3-(2,6-dimethyl-1-piperidinyl)propylamine, following the procedure of Example 21, there is obtained cis-(±)-N-[3-(2,6-dimethyl-1-piperidinyl)propyl]-α-methyl-2-oxo-1-pyrrolidineacetamide; b.p. 165°–170° C./0.1 mm.

EXAMPLE 23

From 8.5 g. of ethyl 2-oxo-1-pyrrolidineacetate and 8.8 g. of 2-(dimethylamino)ethylamine, following the procedure of Example 1, there is obtained N-[2-(dimethylamino)ethyl]-2-oxo-1-pyrrolidineacetamide; b.p. 146°–147° C./0.1 mm.

The hydrochloride salt is obtained following the procedure of Example 1; m.p. 135°–136° C. after recrystallization from 2-propanol.

EXAMPLE 24

From 8.5 g. of ethyl 2-oxo-1-pyrrolidineacetamide and 11.6 g. of N-isopropyl-N-methylethylenediamine, following the procedure of Example 1, there is obtained N-[2-[methyl(1-methylethyl)amino]ethyl]-2-oxo-1-pyrrolidineacetamide; b.p. 152° C./0.07 mm.

EXAMPLE 25

N-[2-[Bis(1-methylethyl)amino]ethyl]-2-oxo-1-pyrrolidineacetamide, 6.02 g. (0.0223 m.) is dissolved in 25 ml. tetrahydrofuran and 0.4 water (0.0223 m.) is added to the solution. After about 5–10 minutes, n-pentane is added in sufficient quantity to stay just short of the point of persistent turbidity. The solution is cooled in an ice bath with seeds present.

Collection by filtration and drying on paper for about 10 minutes yields the monohydrate; m.p. 47°–8° C.

We claim:

1. A compound of the formula

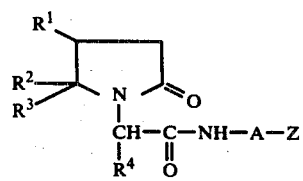

and acid addition salts thereof, wherein $R^1$ is hydrogen or phenyl, $R^2$, $R^3$ and $R^4$ are hydrogen or methyl, A is an alkylene chain having two, three or four carbon atoms which is optionally substituted with one or two methyl or ethyl groups and Z is di(lower alkyl)amino, 4-morpholinyl, 4-(lower alkyl)-1-piperazinyl or (lower alkyl)$_n$-piperidinyl where n is an integer from zero to six with the proviso that when $R^1$ is phenyl, $R^2$ and $R^3$ are hydrogen.

2. The compounds of claim 1 wherein $R^1$ to $R^4$ is hydrogen, A is ethylene or trimethylene and Z is 2,6-dimethylpiperidinyl.

3. The compound of claim 1 having the name cis-N-[2-(2,6-dimethyl-1-piperidinyl)ethyl]-2-oxo-1-pyrrolidineacetamide and acid addition salts thereof.

4. The compound of claim 1 having the same cis-N-[3-(2,6-dimethyl-1-piperidinyl)propyl]-2-oxo-1-pyrrolidineacetamide and acid addition salts thereof.

5. The compound of claim 1 having the name cis-N-[2-(2,6-dimethyl-1-piperidinyl)ethyl]-2-methyl-5-oxo-1-pyrrolidineacetamide and acid addition salts thereof.

6. The compound of claim 1 having the name N-[3-[bis(1-methylethyl)amino]propyl]-2-oxo-4-phenyl-1-pyrrolidineacetamide and acid addition salts thereof.

7. The compound of claim 1 having the name N-[2-[bis(methylethyl)amino]ethyl]-2-oxo-1-pyrrolidineacetamide and acid addition salts thereof.

8. The compound of claim 1 having the name N-[2-(dimethylamino)ethyl]-2-oxo-1-pyrrolidineacetamide and acid addition salts thereof.

9. The compound of claim 1 having the name N-[3-(dimethylamino)propyl]-2-oxo-1-pyrrolidineacetamide and acid addition salts thereof.

10. The compound of claim 1 having the name N-[2-[methyl(1-methylethyl)amino]ethyl]-2-oxo-1-pyrrolidineacetamide and acid addition salts thereof.

11. The compound of claim 1 having the name N-[2-(dimethylamino)ethyl]-2-oxo-1-pyrrolidine-acetamide monohydrochloride.

12. The compound of claim 1 having the name N-[2-[bis(methylethyl)amino]ethyl]-2-oxo-1-pyrrolidineacetamide monohydrate.

* * * * *